United States Patent [19]
Ikeda et al.

[11] Patent Number: 5,985,130
[45] Date of Patent: Nov. 16, 1999

[54] METHOD FOR QUANTIFYING SUBSTRATE

[75] Inventors: Shin Ikeda, Katano; Toshihiko Yoshioka; Shiro Nankai, both of Hirakata, all of Japan

[73] Assignee: Matsushita Electric Industrial Co., Ltd., Osaka, Japan

[21] Appl. No.: 08/834,829

[22] Filed: Apr. 3, 1997

[30] Foreign Application Priority Data

Apr. 4, 1996 [JP] Japan ................................ 8-082631

[51] Int. Cl.$^6$ ............................................. G01N 27/26
[52] U.S. Cl. ...................... 205/777.5; 204/403; 204/406
[58] Field of Search ................................ 204/403, 406, 204/400; 205/777.5; 435/817

[56] References Cited

U.S. PATENT DOCUMENTS

| | | | |
|---|---|---|---|
| 4,045,296 | 8/1977 | Sternberg | 435/11 |
| 4,127,448 | 11/1978 | Schick et al. | 205/777.5 |
| 4,655,880 | 4/1987 | Liu | 205/777.5 |
| 4,767,994 | 8/1988 | Hopkins et al. | 324/438 |
| 4,950,378 | 8/1990 | Nagata | 204/402 |
| 5,378,628 | 1/1995 | Grätzel et al. | 435/288 |

FOREIGN PATENT DOCUMENTS

| | | |
|---|---|---|
| 0 471 986 | 2/1992 | European Pat. Off. . |
| 0 679 720 | 11/1995 | European Pat. Off. . |
| 0 800 080 | 10/1997 | European Pat. Off. . |
| 63-195562 | 12/1988 | Japan . |
| 64-28557 | 1/1989 | Japan . |
| 65-23154 | 1/1989 | Japan . |
| 6-23720 | 3/1994 | Japan . |

OTHER PUBLICATIONS

Proceedings 8th IEEE Instrumentation and Measurement Technology Conference, 1991 month unknown, Institute of Electrical and Electronics Engineers (IEEE CAT No. 91CH2940–5), Fidler, J.C., et al., "A Potentiostat Based On A Voltage–Controlled Current Source For Use With Amperometric Gas Sensors", XP 00295404, pp. 456–459.
European Search Report dated July 25, 1997.

Primary Examiner—T. Tung
Assistant Examiner—Alex Noguerola

[57] ABSTRACT

The present invention provides a method for quantifying a substrate having improved measurement accuracy and measurement sensitivity. According to the method for quantifying the substrate of the present invention, a constant voltage is applied to an electrode system, between a working electrode and a counter electrode, via a resistor connected in series with the electrode system after placing a sample solution containing the substrate on the electrode system, so as to oxidize an electron acceptor, which has been reduced by an enzyme reaction of the substrate, thereby determining a concentration of the substrate included in the sample solution based on an oxidizing current flowing in the course of oxidation.

5 Claims, 3 Drawing Sheets

METHOD FOR QUANTIFYING SUBSTRATE

BACKGROUND OF THE INVENTION

The present invention relates to a method for quantifying a substrate included in a sample solution.

The following describes a method for quantifying glucose as one example of the substrate.

As a conventional electrochemical method for quantifying glucose, a method which employs a combination of a reaction layer including glucose oxidase (EC1.1.3.4, hereinafter referred to as GOD) with an oxygen electrode or a hydrogen peroxide electrode is well known (for example, 'Bio-sensor' edited by Shuichi SUZUKI, Kodansha).

GOD uses oxygen as an electron acceptor and selectively oxidizes the substrate, β-D-glucose, to D-glucono-δ-lactone. Accompanied by this reaction, oxygen is reduced to hydrogen peroxide. The amount of glucose is determined by measuring the amount of consumed oxygen with the oxygen electrode or alternatively measuring the amount of generated hydrogen peroxide with the hydrogen peroxide electrode.

However, as presumed from the reaction process mentioned above, the result of this method is significantly affected by a concentration of oxygen dissolved in a sample solution. Especially, measurement is even impossible under an oxygen-free condition.

Novel glucose sensors have accordingly been developed, in which an organic compound or a metal complex, such as potassium ferricyanide, a ferrocene derivative or a quinone derivative is used in place of oxygen as the electron acceptor. This type of sensor oxidizes the electron acceptor, which has been reduced by an enzyme reaction, with the electrode and determines a concentration of glucose based on its oxidizing current. This system enables known amounts of GOD and the electron acceptor to be stably and accurately carried on a electrode system, and to integrate the electrode system and a reaction layer in a state similar to the dry state. Disposable glucose sensors based on this technique can readily determine a concentration of glucose only by introducing a sample into a sensor chip connected to a measurement device, and accordingly have been noted recently. This technique is applicable not only to a quantification of glucose but to a quantification of another substrate, and is extensively studied. This technique, which utilizes such an electron acceptor and integrates the electrode system and the reaction layer, enables simple electrochemical quantification of the substrate.

For the quantification of the substrate, such as blood sugar value, a novel quantifying method with high accuracy has been highly demanded.

BRIEF SUMMARY OF THE INVENTION

The object of the present invention is thus to provide a novel method for quantifying a substrate with improved accuracy and sensitivity.

The present invention provides a method for quantifying a substrate, which places a sample solution containing a substrate on an electrode system composed of a working electrode and a counter electrode, and then applies a constant voltage to the electrode system via a resistor connected in series with the electrode system. By application of the voltage, an electron acceptor which has been reduced by an enzyme reaction of the substrate is oxidized. A concentration of the substrate included in the sample solution is quantified based on an oxidizing current flowing in the course of oxidation.

The present invention is directed to a method for quantifying a substrate, which comprises the steps of:

bringing a solution containing an enzyme into contact with a surface of an electrode system composed of a working electrode and a counter electrode;

adding a sample solution containing a substrate to the solution containing the enzyme;

applying a constant voltage to the electrode system via a resistor connected in series with the electrode system; and measuring an electric current flowing through the electrode system.

In accordance with one preferable mode of the present invention, a solution containing an electron acceptor is further added to the enzyme solution in the step of adding the sample solution to the solution containing the enzyme.

The present invention is also directed to another method for quantifying a substrate, which comprises the steps of:

adding a sample solution containing a substrate to a reaction layer formed on a surface of an electrode system composed of a working electrode and a counter electrode, the reaction layer including an enzyme;

applying a constant voltage to the electrode system via a resistor connected in series with the electrode system; and measuring an electric current flowing through the electrode system.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

The method for quantifying a substrate of the present invention lowers a potential on a working electrode in the process of applying a voltage to the electrode system so as to delay a progress of oxidation of an electron acceptor which has been reduced, thereby enhancing concentration of the reduced electron acceptor remaining still after elapse of a desired time period. In the method for quantifying a substrate of the present invention, the voltage is applied to the electrode system via a resistor connected in series with the electrode system. Since voltage drop is required to attain the above effects, the resistance of not less than 1 kΩ is preferable as a concrete example. The applied voltage and the time period until beginning of measuring an oxidizing current are set appropriately by taking into account a type and concentration of the substrate to be measured.

In the method for quantifying a substrate of the present invention, potassium ferricyanide, p-benzoquinone, phenazine methosulfate, methylene blue, and a ferrocene derivative can be used as the electron acceptor. Of course, similar effects are obtained in a case that oxygen is used as the electron acceptor. Available enzymes in this method include glucose oxidase, lactate oxidase, cholesterol oxidase, xanthine oxidase and the like.

A sensor having a hydrophilic polymer layer formed on the electrode system enables determination of the substrate with high accuracy. Available hydrophilic polymers include carboxymethylcellulose (hereinafter referred to as CMC), polyvinyl alcohols, polystyrene sulfonates, and polyamino acids such as polylysine. Even in a case that the sensor does not have the hydrophilic polymer layer, the system with load of resistor enables quantification of the substrate with higher accuracy, compared with the system without any resistor.

The principle of the present invention is applicable to various types of sensors, for example, a sensor in which a reaction reagent containing an enzyme and an electron acceptor is dissolved in a sample solution and another sensor in which a sample solution is added to a reaction layer formed in advance to have a fixed reaction reagent.

As examples of the present invention, concrete methods for quantifying glucose, wherein a resistor is directly connected with an electrode system, are described in detail with reference to the attached drawings.

EXAMPLE 1

Two carbon bars were embedded in parallel to each other in polytetrafluoroethylene and cut in round slices. A pair of exposed carbon bar slices were used as an electrode system, a working electrode and a counter electrode of a glucose sensor.

Figure 1:
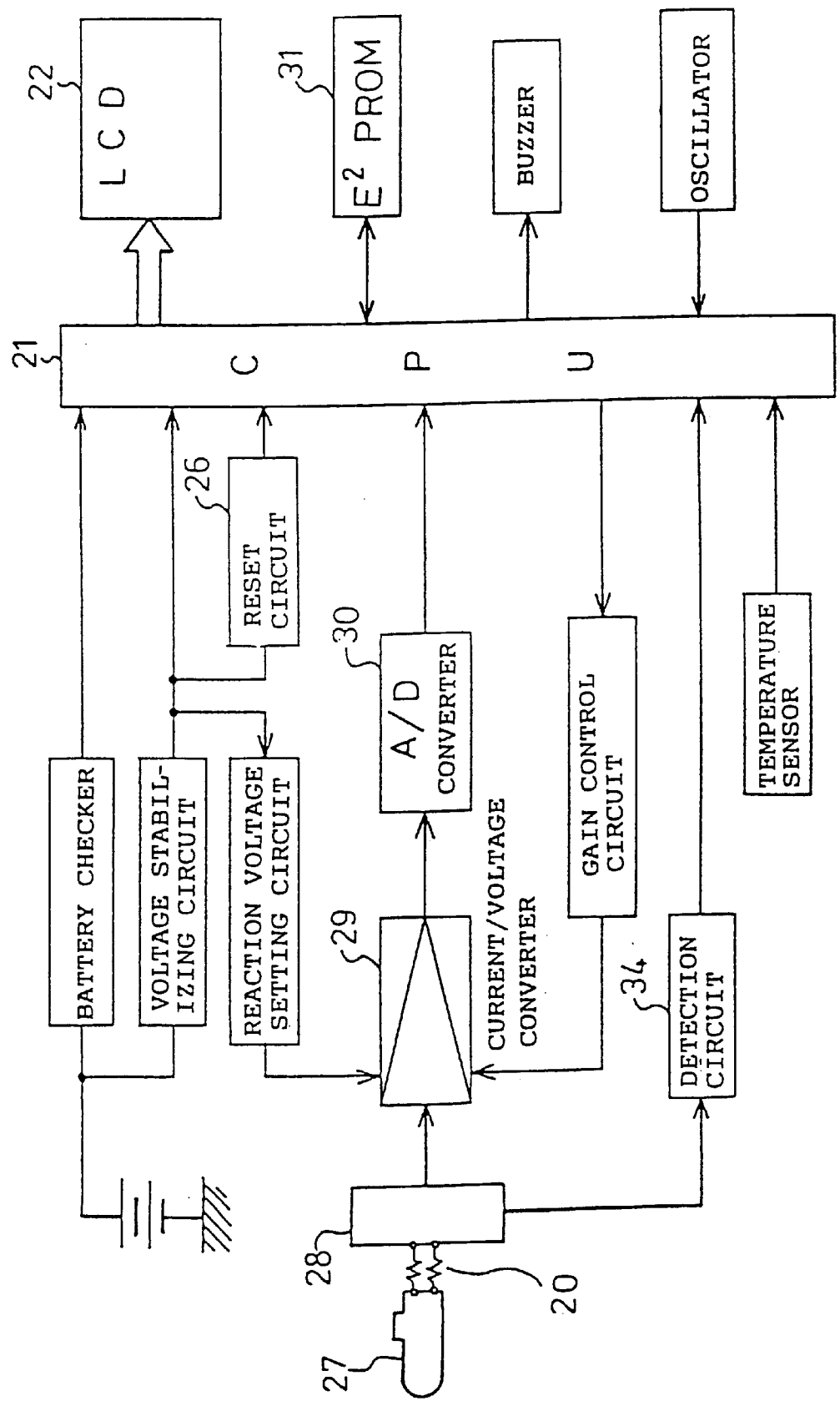
FIG. 1 schematically illustrates a measurement system used for quantification of glucose in one embodiment of the present invention.

The concentration of glucose was measured in the following manner with a measurement system shown in FIG. 1.

The glucose sensor 27 and a connector 28 were connected to each other via resistors 20 of 10 kΩ. The one resistor 20 is installed between a lead linked with the working electrode and a connection terminal of the connector 28. The other resistor 20 is installed between a lead linked with the counter electrode and another connection terminal of the connector 28.

A phosphate buffer solution containing GOD as an enzyme and potassium ferricyanide as an electron acceptor was added dropwise to an electrode system of the glucose sensor 27, and a sample solution containing glucose as the substrate was further added dropwise to the same place. When 55 seconds elapsed since the drop of the substrate, a voltage of 800 mV on the basis of the voltage at the counter electrode was applied to the working electrode via the resistors 20. The electric current flowing through the electrode system was measured 5 seconds after application of the voltage.

Application of the voltage to the electrode system oxidizes the electron acceptor, which has been reduced in the process of an enzyme reaction of glucose, and thereby generates an oxidizing current which flows from the working electrode to the counter electrode. The oxidizing current is measured with a detection circuit 34 and converted to a voltage signal by a current/voltage converter 29. The converted voltage signal is further converted to a digital signal by an A/D converter 30. A CPU 21 carries out an arithmetic operation of the input digital signal and outputs the result of the arithmetic operation to an LCD 22 while storing the result into a memory 31.

A response of an electric current depending upon a concentration of glucose in the sample solution was obtained as a result of this measurement.

COMPARATIVE EXAMPLE 1

As a comparative example, a similar measurement was carried out with the same measurement system wherein the glucose sensor 27 and the connector 28 were connected to each other not via the resistors but directly. A response of an electric current depending upon a concentration of glucose in the sample solution was also obtained as a result of this measurement.

In comparison between a gradient of current/glucose concentration of the linear response range obtained in Example 1 with the resistor loading and the one obtained in Comparative Example 1 without any resistor, it was recognized that loading of resistors increased the gradient by 15%.

Another measurement using platinum as an electrode material and measuring hydrogen peroxide generated as a result of an enzyme reaction showed a similar dependence of resistor loading.

EXAMPLE 2

Figure 2:
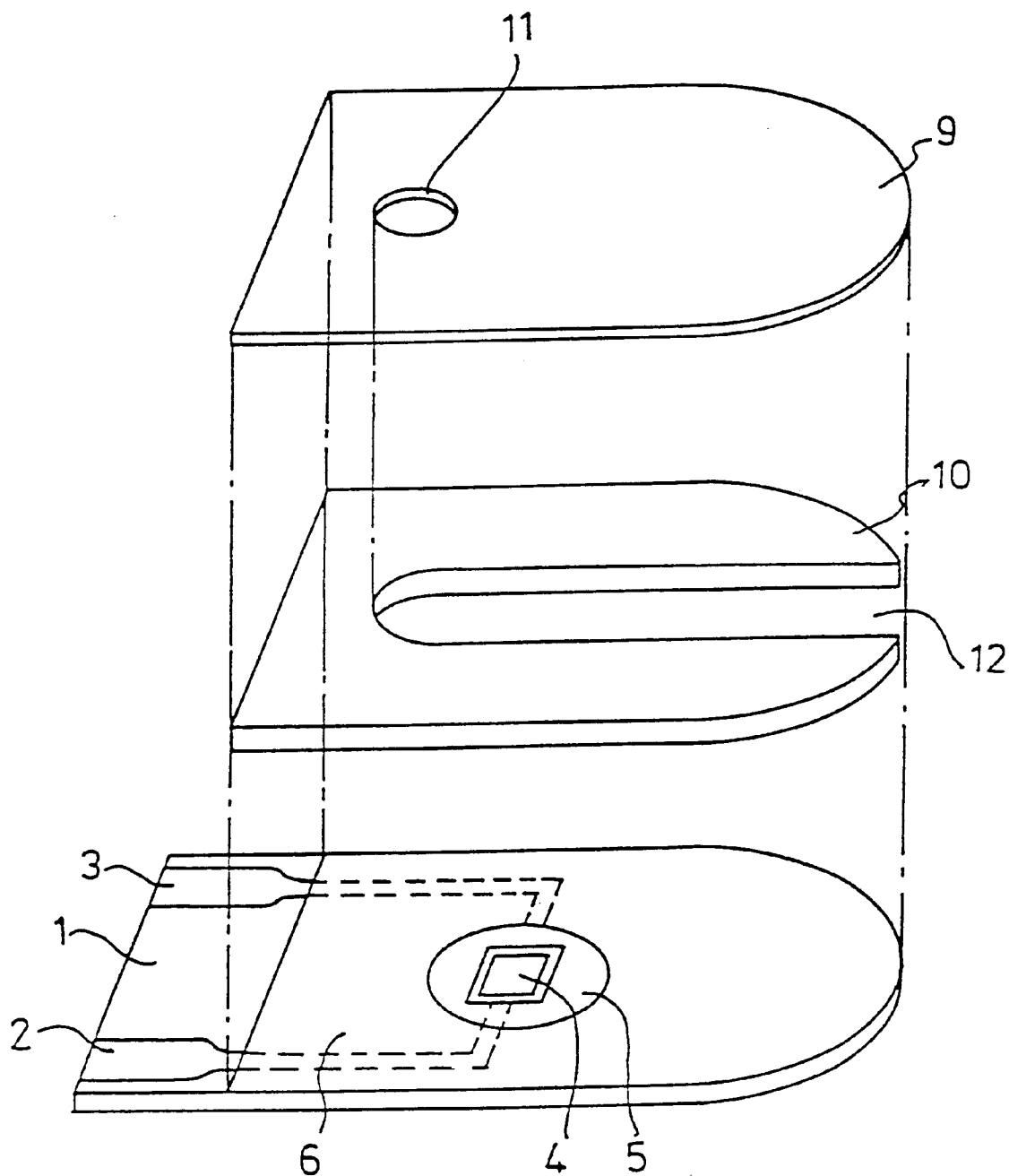
FIG. 2 is an exploded perspective view of a glucose sensor for quantification of glucose omitting a reaction layer prepared in one embodiment of the present invention.
Figure 3:
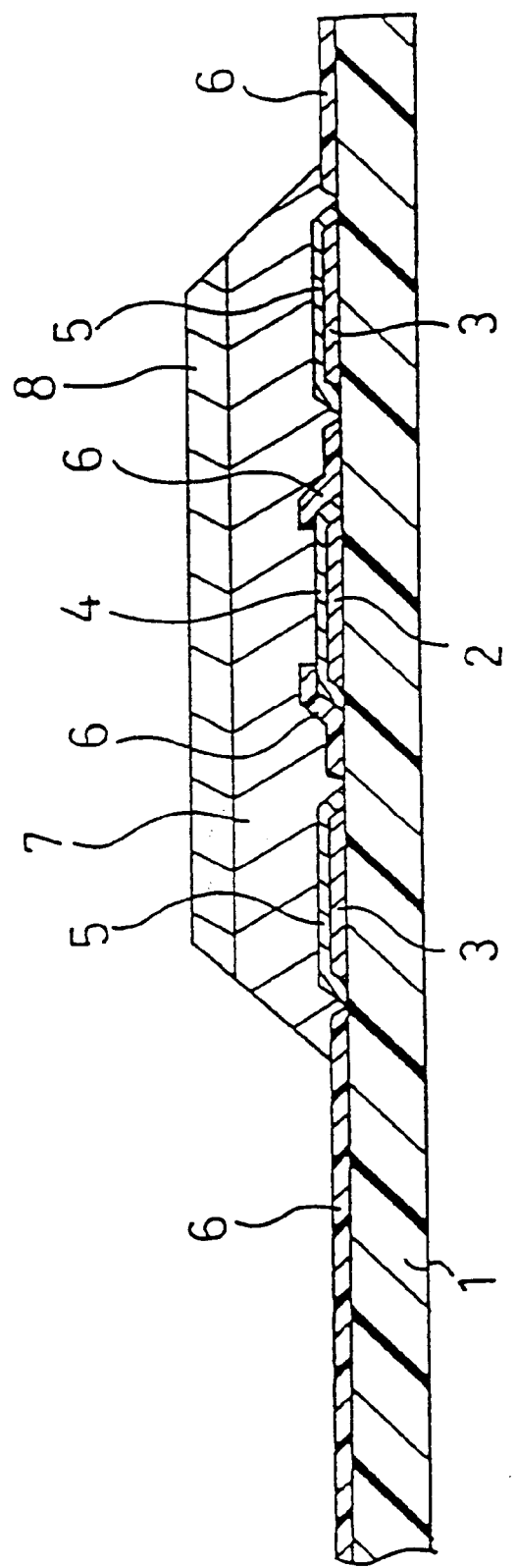
FIG. 3 is a vertical cross-sectional view illustrating the glucose sensor omitting a spacer.

FIG. 2 shows an exploded perspective view of a disposable glucose sensor used in this example omitting a reaction layer. FIG. 3 shows a vertical cross-sectional view of the same glucose sensor omitting a cover 9 and a spacer 10. An insulating base plate 1 is composed of polyethylene terephthalate and has leads 2 and 3 formed by screen printing a silver paste on the surface thereof. A working electrode 4 is formed by printing an electrically conductive carbon paste including a resin binder after the formation of the leads 2 and 3. The working electrode 4 is connected to the lead 2.

An insulating layer 6 is then formed by printing an insulating paste that is primarily composed of, for example, polytetrafluoroethylene. The insulating layer 6 covers a periphery of the working electrode 4 and accordingly keeps an area of an exposed portion of the working electrode 4 constant. The insulating layer 6 also covers the leads 2 and 3 partly.

A counter electrode 5 is formed by printing the carbon paste with a resin binder to come into contact with the lead 3.

An aqueous solution of CMC is added dropwise to the electrode system composed of the working electrode 4 and the counter electrode 5 and then dried, so as to form a CMC layer. An aqueous solution containing glucose oxidase as the enzyme and potassium ferricyanide as the electron acceptor is added dropwise to the electrode system and dried, so as to form a reaction layer 7 partly mixed with the CMC layer.

A lecithin layer 8 is formed on the surface of the reaction layer 7 by spreading an organic solvent solution of lecithin, for example, a toluene solution of lecithin, supplied from a sample supply portion (disposed on a tip of the sensor) over the reaction layer 7 and drying the lecithin solution. The lecithin layer 8 ensures a smooth supply of a sample solution onto the reaction layer 7. A cover 9 and a spacer 10 are then adhered to each other to satisfy the positional relationship shown by the one-dot chain lines in FIG. 2. This completes a glucose sensor.

A similar measurement to that of Example 1 was carried out with the glucose sensor thus obtained. This glucose sensor and the connector 28 were connected to each other via resistors 20 of 10 kΩ. The one resistor 20 is installed between a lead linked with the working electrode 4 and a connection terminal of the connector 28. The other resistor 20 is installed between a lead 3 linked with the counter electrode 5 and another connection terminal of the connector 28. As a sample solution, 3 μl of a glucose solution was supplied to this sensor from a sample supply aperture 12. The sample solution reached an air hole 11 and the reaction layer on the electrode system was dissolved. A voltage of 800 mV on the basis of the voltage at the counter electrode was applied to the working electrode via the resistors 20, 55 seconds after supply of the sample solution, and an oxidizing current was measured 5 seconds after application of the voltage. The response of electric current depending upon a concentration of glucose in the sample solution was obtained as a result of this measurement.

COMPARATIVE EXAMPLE 2

As a comparative example, a similar measurement was carried out with the same system wherein the glucose sensor 27 and the connector 28 were connected to each other directly. A response of an electric current depending upon a concentration of glucose in the sample solution was also obtained as a result of this measurement.

In comparison between a gradient of current/glucose concentration of a linear response range obtained in Example 2 with the resistor loading and the one obtained in Comparative Example 2 without any resistor, it was recognized that loading of the resistor increased the gradient by 15%.

The reason why a sensor response was enhanced in Examples 1 and 2 has not been elucidated. It is, however, considered that loading the resistor forcibly causes a voltage drop and delays a time when a potential on the electrode reaches a sufficient value for the electrode reaction. When a voltage is applied to the electrode system, oxidation occurs on the working electrode while reduction occurs on the counter electrode. This lowers a potential on the counter electrode. Since a potential difference between the working electrode and the counter electrode is constant, the potential on the working electrode varies with a variation in potential on the counter electrode. It is thought that the possible range of the potential on the working electrode significantly affects an amount of reduced electron acceptors which is oxidized in a predetermined time period prior to the measurement of an oxidizing current.

Actually, a potential on a counter electrode with respect to a silver/silver chloride electrode was measured with a sensor similar to that of Example 2.

The sensor was directly connected to the connector. The potential on the counter electrode was 250 mV before application of a voltage, lowered to 0 mV immediately after application of the voltage of 800 mV between the counter electrode and a working electrode, and was recovered to 152 mV after 5 seconds. An application of a voltage causes a reduction on the counter electrode and accordingly lowers the potential on the counter electrode. With a progress of an electrode reaction, an amount of reaction decreases, and the potential on the counter electrode is gradually recovered. Even when the voltage was applied, the potential difference between the counter electrode and the working electrode was always 800 mV. Therefore, the potential on the working electrode was varied from 800 mV to 952 mV in 5 seconds after application of the voltage.

When resistors of 10 kΩ were connected between a pair of leads of the sensor and a pair of connection terminals of the connector, the voltage drop due to the resistors lowered the potential on the working electrode to 578 mV immediately after the application of the voltage, which was recovered to 850 mV in 5 seconds after the application of the voltage.

Connection of the resistors lowered the potential on the working electrode, compared with that in the case without the resistors. This phenomenon is remarkably observed immediately after the application of the voltage. In a case that no resistor is connected, an electrode reaction is dominated by a diffusion process of a dissolved substance in the voltage range. The electrode response is accordingly not affected by the potential on the working electrode and the reaction proceeds smoothly. In a case that the resistors are connected, on the other hand, a low potential does not set the diffusion process as rate-determining stage and the reaction proceeds relatively slowly. However, it is considered that a reaction rate is enhanced with an increase in potential on the working electrode, and the diffusion process reaches the rate-determining stage after 5 seconds. This difference in progress of the reaction for 5 seconds causes the concentration of a remaining reduced electron acceptor after 5 seconds to be higher in a case with connection of the resistors than that in a case without the resistors. This increases the oxidizing current measured after elapse of a predetermined time period. The higher the concentration of the substrate, the larger the difference in an amount of the oxidizing current. Therefore, connection of the resistors improves measurement sensitivity as well as measurement accuracy.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is,intended that the appended claims be interpreted as covering all alterations and modifications as fall within the true spirit and scope of the invention.

The entire disclosure of Japanese Patent Application No. Hei 08-082631 filed on Apr. 4, 1996 including specification, claims, drawings and summary is incorporated herein by reference in its entirety.

What is claimed is:

1. A method for quantifying a substrate comprising the steps of:

bringing a solution containing an enzyme and an electron acceptor into contact with a surface of an electrode system comprising a working electrode and a counter electrode;

adding a sample solution containing a substrate to said solution containing the enzyme and the electron acceptor;

connecting said electrode system to a constant voltage source via a resistor being connected in series to said working electrode in order to apply to said electrode system a voltage which exhibits a temporary drop at said working electrode; and measuring an electric current flowing through said electrode system for a predetermined time after the application of said voltage.

2. The method for quantifying a substrate in accordance with claim 1, wherein said resistor has a resistance of not less than 1 kΩ.

3. A method for quantifying a substrate comprising the steps of:

adding a sample solution containing a substrate to a reaction layer formed on a surface of an electrode system comprising a working electrode and a counter electrode, said reaction layer containing an enzyme and an electron acceptor;

connecting said electrode system to a constant voltage source via a resistor being connected in series to said working electrode in order to apply to said electrode system a voltage which exhibits a temporary drop at said working electrode; and measuring an electric current flowing through said electrode system for a predetermined time after the application of said voltage.

4. The method for quantifying a substrate in accordance with claim 3, wherein said reaction layer further contains a hydrophilic polymer.

5. The method for quantifying a substrate in accordance with claim 3, wherein said resistor has a resistance of not less than 1 kΩ.

* * * * *